United States Patent
Piskun et al.

(10) Patent No.: US 11,896,323 B2
(45) Date of Patent: Feb. 13, 2024

(54) SYSTEM, METHOD, AND COMPUTER-ACCESSIBLE MEDIUM FOR AUTOMATICALLY TRACKING AND/OR IDENTIFYING AT LEAST ONE PORTION OF AN ANATOMICAL STRUCTURE DURING A MEDICAL PROCEDURE

(71) Applicant: Aibolit Technologies, LLC, Delray Beach, FL (US)

(72) Inventors: Gregory Piskun, Delray Beach, FL (US); Stefanin Aleksandr, Mogilev (BY); Kotau Vasil, Minsk (BY); Hancharyk Aliaksei, Minsk (BY); Shingel Alexander, Minsk (BY); Vasil Boika, Delray Beach, FL (US)

(73) Assignee: AIBOLIT TECHNOLOGIES, LLC, Delray Beach, FL (US)

( * ) Notice: Subject to any disclaimer, the term of this patent is extended or adjusted under 35 U.S.C. 154(b) by 226 days.

(21) Appl. No.: 17/462,774

(22) Filed: Aug. 31, 2021

(65) Prior Publication Data
US 2022/0093236 A1 Mar. 24, 2022

Related U.S. Application Data

(60) Provisional application No. 63/073,020, filed on Sep. 1, 2020.

(51) Int. Cl.
*A61B 34/00* (2016.01)
*A61B 1/00* (2006.01)
*G06T 7/00* (2017.01)

(52) U.S. Cl.
CPC ........ *A61B 34/25* (2016.02); *A61B 1/000096* (2022.02); *G06T 7/0012* (2013.01)

(58) Field of Classification Search
CPC .. G06T 7/0012; A61B 1/000096; A61B 34/25
See application file for complete search history.

(56) References Cited

U.S. PATENT DOCUMENTS

| | | | |
|---|---|---|---|
| 6,810,281 B2 * | 10/2004 | Brock | A61B 5/24 600/407 |
| 7,892,232 B2 * | 2/2011 | Boese | A61B 18/1492 606/41 |

(Continued)

FOREIGN PATENT DOCUMENTS

WO 2019195926 A1 10/2019

OTHER PUBLICATIONS

International Search Report and Written Opinion for International Patent Application No. PCT/US2021/048666 dated Jan. 21, 2022.

(Continued)

*Primary Examiner* — Michael I Ezewoko
(74) *Attorney, Agent, or Firm* — Hunton Andrews Kurth LLP

(57) ABSTRACT

Exemplary system, method, and computer-accessible medium can be provided for effectuating a video overlay during a medical procedure(s) performed on a patient(s) can include, for example, receiving a live video(s) of the medical procedure(s) performed on the patient(s), identifying, in real time, a target area(s), an area of danger(s) and/or at least partially obscured anatomical structures of significance on a patient's anatomy by applying a machine learning procedure to the live video(s), and providing the video overlay based on the identification of the target area(s) and the area of danger(s). The video overlay can be continuously modified, in real-time, using the machine learning procedure. The medical procedure(s) can be a gallbladder surgery. The machine learning procedure can include a neural network, which can be a convolutional neural network.

16 Claims, 12 Drawing Sheets
(9 of 12 Drawing Sheet(s) Filed in Color)

(56) References Cited

U.S. PATENT DOCUMENTS

| | | | | |
|---|---|---|---|---|
| 8,294,716 | B2* | 10/2012 | Lord | A61B 5/00 |
| | | | | 345/440 |
| 9,295,372 | B2 | 3/2016 | Staples, II et al. | |
| 9,843,596 | B1* | 12/2017 | Averbuch | G06F 21/554 |
| 10,187,409 | B1* | 1/2019 | Averbuch | G06F 21/55 |
| 10,251,714 | B2 | 4/2019 | Carnes et al. | |
| 10,333,953 | B1* | 6/2019 | Averbuch | G06F 21/554 |
| 10,383,694 | B1 | 8/2019 | Venkataraman et al. | |
| 10,694,963 | B2* | 6/2020 | Van Langenhove | |
| | | | | A61B 6/5217 |
| 10,729,502 | B1* | 8/2020 | Wolf | G16H 20/40 |
| 10,762,398 | B2* | 9/2020 | Sjölund | G06V 10/454 |
| 10,886,015 | B2* | 1/2021 | Wolf | B25J 9/1661 |
| 10,943,682 | B2* | 3/2021 | Wolf | G16H 50/30 |
| 11,017,106 | B2* | 5/2021 | Evans | G06F 21/6218 |
| 11,065,079 | B2* | 7/2021 | Wolf | G06F 16/735 |
| 11,116,587 | B2* | 9/2021 | Wolf | G06F 3/048 |
| 11,304,686 | B2* | 4/2022 | Manzke | A61B 5/061 |
| 11,348,246 | B2* | 5/2022 | Phogat | G06T 11/206 |
| 11,369,435 | B2* | 6/2022 | Khan | A61B 90/50 |
| 11,380,431 | B2* | 7/2022 | Wolf | G16H 20/40 |
| 11,426,255 | B2* | 8/2022 | Wolf | A61B 34/70 |
| 11,436,837 | B2* | 9/2022 | Pham | G06T 7/11 |
| 11,452,576 | B2* | 9/2022 | Wolf | A61B 1/000096 |
| 11,484,384 | B2* | 11/2022 | Wolf | G16H 50/20 |
| 11,701,176 | B2* | 7/2023 | Redmond | A61B 34/10 |
| | | | | 606/279 |
| 2007/0066899 | A1* | 3/2007 | Boese | A61B 18/1492 |
| | | | | 606/41 |
| 2009/0231341 | A1* | 9/2009 | Lord | A61B 5/7445 |
| | | | | 600/300 |
| 2011/0046476 | A1 | 2/2011 | Cinquin et al. | |
| 2014/0142422 | A1* | 5/2014 | Manzke | A61B 8/12 |
| | | | | 600/424 |
| 2014/0228632 | A1 | 8/2014 | Sholev et al. | |
| 2015/0065803 | A1 | 3/2015 | Douglas et al. | |
| 2015/0238276 | A1 | 8/2015 | Atarot et al. | |
| 2016/0019716 | A1* | 1/2016 | Huang | G16Z 99/00 |
| | | | | 345/633 |
| 2018/0247023 | A1 | 8/2018 | Divine et al. | |
| 2019/0175272 | A1* | 6/2019 | Khan | A61B 17/16 |
| 2019/0297276 | A1 | 9/2019 | Sachdev et al. | |
| 2019/0385302 | A1 | 12/2019 | Ngo Dinh et al. | |
| 2020/0035348 | A1 | 1/2020 | Sartor et al. | |
| 2020/0069192 | A1* | 3/2020 | Sanborn | A61B 5/015 |
| 2020/0237452 | A1* | 7/2020 | Wolf | G06F 3/048 |
| 2020/0268469 | A1* | 8/2020 | Wolf | A61B 1/015 |
| 2020/0268472 | A1* | 8/2020 | Wolf | A61B 17/00 |
| 2020/0272660 | A1* | 8/2020 | Wolf | G06Q 10/06312 |
| 2020/0273548 | A1* | 8/2020 | Wolf | A61B 34/25 |
| 2020/0273552 | A1* | 8/2020 | Wolf | B25J 9/1661 |
| 2020/0273557 | A1* | 8/2020 | Wolf | A61B 1/000094 |
| 2020/0273560 | A1* | 8/2020 | Wolf | G16H 70/20 |
| 2020/0273561 | A1* | 8/2020 | Wolf | G16H 30/40 |
| 2020/0273563 | A1* | 8/2020 | Wolf | A61B 34/30 |
| 2020/0273575 | A1* | 8/2020 | Wolf | G16H 20/40 |
| 2020/0273577 | A1* | 8/2020 | Wolf | G06F 16/71 |
| 2020/0273581 | A1* | 8/2020 | Wolf | A61B 1/000096 |
| 2021/0186644 | A1* | 6/2021 | Schmitt | A61G 13/10 |
| 2021/0212776 | A1* | 7/2021 | Schmitt | A61B 90/50 |
| 2021/0298869 | A1* | 9/2021 | Wolf | A61B 34/70 |
| 2021/0315632 | A1* | 10/2021 | Holman | A61B 18/14 |
| 2022/0057519 | A1* | 2/2022 | Goldstein | G01S 17/04 |
| 2022/0106370 | A1* | 4/2022 | Locke | A61K 39/00115 |
| 2022/0180528 | A1* | 6/2022 | Dundar | G06N 20/00 |
| 2022/0301674 | A1* | 9/2022 | Wolf | A61B 34/30 |
| 2022/0346875 | A1* | 11/2022 | Khan | A61B 34/10 |

OTHER PUBLICATIONS

X. Zhao et al. "Artificial Intelligence in Surgery," Frontiers of Medicine, pp. 16-18, Jan. 6, 2020.

L. Chen et al. "Recent Developments and Future Challenges in Medical Mixed Reality," Proceedings of 16th IEEE International Symposium on Mixed and Augmented Reality (ISMAR), Aug. 3, 2017.

* cited by examiner

SYSTEM, METHOD, AND COMPUTER-ACCESSIBLE MEDIUM FOR AUTOMATICALLY TRACKING AND/OR IDENTIFYING AT LEAST ONE PORTION OF AN ANATOMICAL STRUCTURE DURING A MEDICAL PROCEDURE

CROSS-REFERENCE TO RELATED APPLICATION(S)

The present application relates to and claims priority from U.S. Patent Application No. 63/073,020 filed on Sep. 1, 2020, the entire disclosure of which is incorporated herein by reference.

FIELD OF THE DISCLOSURE

The present disclosure relates generally to anatomical structure tracking, and more specifically, to exemplary embodiments of exemplary systems, methods, and computer-accessible mediums for automatically tracking and/or identifying at least one portion of an anatomical structure during a medical procedure.

BACKGROUND INFORMATION

Laparoscopic or "minimally invasive" surgery is a specialized technique for performing surgery. Various medical procedures can be performed laparoscopically, including gynecologic surgery, gall bladder surgery, and intestinal surgery, just to name a few. In traditional "open" surgery, the surgeon typically uses a single incision to enter into the abdomen. In contrast, laparoscopic procedure can use small incisions (e.g., 0.5-1 cm incisions). Each incision is called a "port," and at each port, a tubular instrument known as a trochar is inserted. Specialized instruments and cameras (e.g., referred to as a laparoscope) are passed through the trochars during the procedure. The laparoscope transmits images from the abdominal cavity to high-resolution video monitors in the operating room. During the operation, the surgeon watches detailed images of the abdomen on the monitor. This system allows the surgeon to perform the same operations as traditional surgery but with smaller incisions. However, for certain types of surgeries, the surgical site, or anatomical structures at the surgical site can be obfuscated. For example, during gallbladder surgery, certain anatomical structures are hidden from view, including certain structures, which if accidentally cut or punctured, can cause significant injury to the patient.

Laparoscopic cholecystectomy is a commonly performed surgical operation. Although the complications are relatively rare, certain complications related to the intraoperative biliary injury can be extremely devastating for patients, surgeons, and healthcare systems. A cause of these complications can include, for example, the surgeon's inadvertent misidentification of the surgical anatomy.

The natural anatomy, as seen on the laparoscopic display during laparoscopic surgery in real-time, does not have clearly identified (e.g., colored or otherwise defined) structures and regions, as is typically seen in the anatomical atlas for the medical trainees. Further, critically important structures, such as bile ducts and vessels, are normally obscured by the normal or pathological covering layers of the connective, scar, and fatty tissue, which require surgeons to first remove those coverings (e.g., using exploratory dissecting movements) in order to uncover the targeted anatomical structures. The naturally occurring numerous anatomical variations further challenges the identification of the targeted anatomical structures. In addition, the natural subtle colors, or the lack of thereof, of the important anatomical structures in this region can facilitate a surgeon's cognitive errors or misidentification of the critically important surgical anatomy.

Currently, there is a steep learning to become proficient in the prediction and the accurate early recognition of the critical anatomical structures for a safe performance of laparoscopic cholecystectomy. Inexperienced surgeons more often make cognitive mistakes, leading to complications. Even experienced surgeons can make mistakes when tired, when encountering an unfamiliar anatomical variation, and/or when their cognitive acuity is otherwise affected.

Thus, it may be beneficial to provide exemplary systems, methods, and computer-accessible mediums for automatically tracking and/or identifying an anatomical structure during a medical procedure, which can overcome at least some of the deficiencies described herein above.

SUMMARY OF EXEMPLARY EMBODIMENTS

Exemplary system, method, and computer-accessible medium can be provided for providing or facilitating a video overlay during a medical procedure(s) performed on a patient(s) can include, for example, receiving a live video(s) of the medical procedure(s) performed on the patient(s), identifying, in real time, a target area(s) and an area of danger(s) on an anatomical structure(s) of the patient(s) by applying a machine learning procedure to the live video(s), and providing the video overlay based on the identification of the target area(s) and the area of danger(s). The video overlay can be continuously modified, in real-time, using the machine learning procedure. The medical procedure(s) can be a gallbladder surgery. The machine learning procedure can include a neural network, which can be a convolutional neural network.

In some exemplary embodiments of the present disclosure, the machine learning procedure can be trained using (i) a plurality of further videos, or (ii) a plurality of images. The frames can be shifted, scaled, sheared, rotated, or flipped. A safe to manipulate anatomical structure(s) can be identified in the live video(s) using the machine learning procedure. A marker(s) associated with the medical procedure(s) can be determined. An indication can be provided to a medical professional(s) based on the marker(s). The indication can be a safe-to-proceed indication if the marker(s) can be detected, or a not-safe-to-proceed indication can be provided if the marker(s) cannot be detected.

Additionally, an exemplary system, method, and computer-accessible medium for providing or facilitating a video overlay during a medical procedure(s) performed on a patient(s) can include receiving a live video(s) of the medical procedure(s) performed on the patient(s), identifying, in real time, a location of an anatomical structure(s) that is at least partially obscured from a human eye or a visualization tool by applying a machine learning procedure to the video(s), and providing the video overlay based on the identification of the obscured anatomical structure(s). The anatomical structure(s) can be a wholly obscured from the human eye or the visualization tool. The identifying the location of the anatomical structure(s) can include predicting a location of the anatomical structure(s). The video overlay can be continuously modified, in real-time, using the machine learning procedure.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objects, features and advantages of the present disclosure will become apparent from the following detailed description taken in conjunction with the accompanying Figures showing illustrative embodiments of the present disclosure, in which.

Figure 1:
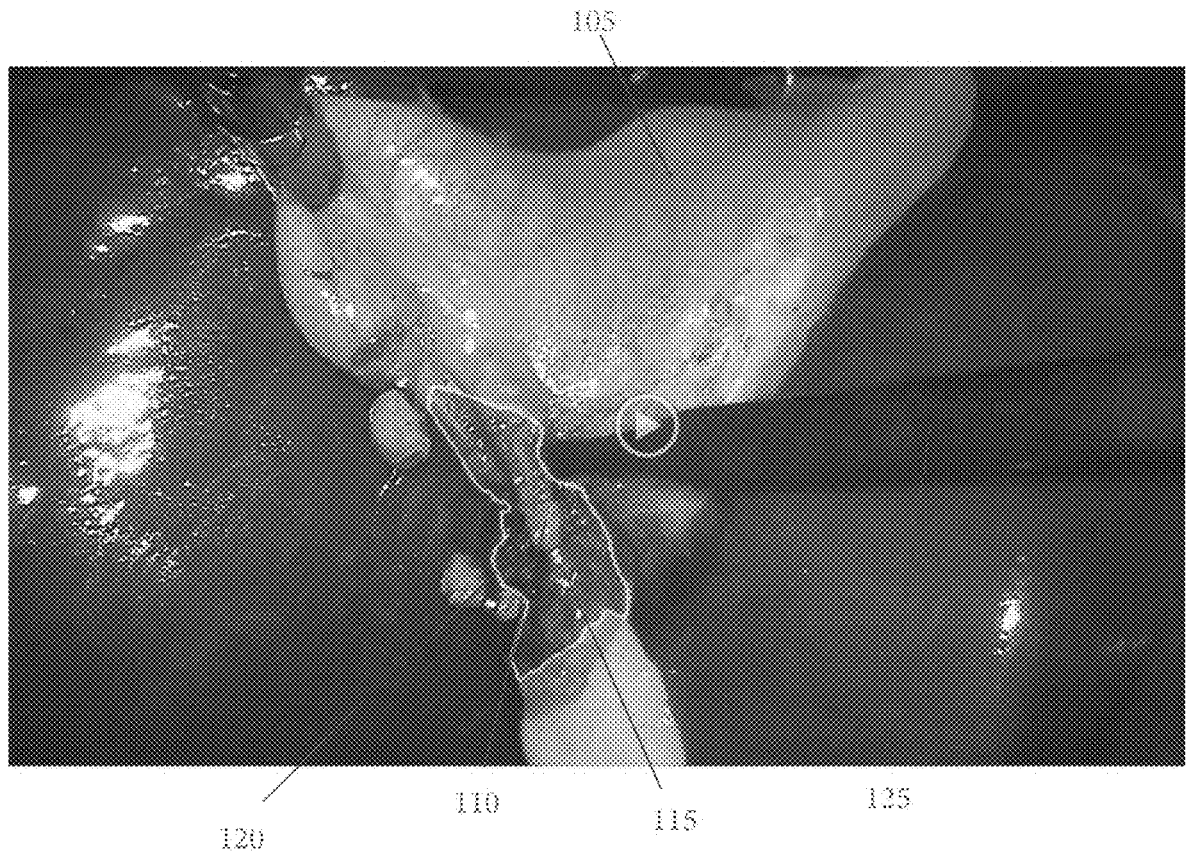
FIGS. 1-4 are exemplary images of a video overlay generated, in real time, during a surgery according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method, and computer-accessible medium, according to an exemplary embodiment of the present disclosure, can be used to identify and/or track a surgical target zone, surgical danger zone and anatomical structures of significance, for example, cystic duct and cystic artery, in the subhepatic area of a patient's body on the display during laparoscopic gallbladder procedure. According to an exemplary embodiment of the present disclosure, a video (e.g., a real time video) can be received, that can include an anatomical region (e.g., a gallbladder region and surrounding anatomical structures). The exemplary system, method, and computer-accessible medium can analyze and/or process the video to identify the gallbladder region and surrounding anatomical structures, the surgical target zone, the surgical danger zone, and the anatomical structures of surgical significance. Additionally, the exemplary system, method, and computer-accessible medium can automatically extract anatomical features based on imaging data, and predict the location of the anatomical structures of surgical significance, such as, for example, a cystic duct and a cyst artery, before they are clearly seen on the display by the human eye (e.g., by the surgeon performing the surgical procedure). Further, the exemplary system, method, and computer-accessible medium, according to an exemplary embodiment of the present disclosure, can be trained from data from a plurality of laparoscopic cholecystectomy videos, and can provide predictive markings of the anatomical regions and specific anatomical structures or portions thereof in real-time on the laparoscopic video display during a laparoscopic cholecystectomy. The markings can be transparent highlights, which can be, for example, superimposed on the anatomy of interest (e.g., transparent punctate lines for predicting the anatomy and transparent solid lines for the identified anatomy) or portions thereof, while not interfering with the surgical video.

FIGS. 1-4 show exemplary images of a video overlay generated, in real time, during a medical (e.g., surgical) procedure according to an exemplary embodiment of the present disclosure. The medical/surgical procedure can be or include the removal of an organ (e.g., a gallbladder) or any other surgical procedure performed using a camera. For example, one or more processors used with and/or by the exemplary system, method, and computer-accessible medium, according to an exemplary embodiment of the present disclosure, can receive a live video of a medical/surgical procedure (e.g., a laparoscopic surgical procedure), and in real time, provide the surgeon or another medical professional with an overlay over the video. As shown in FIG. 1, one or more computer processors used with and/or by the exemplary system, method, and computer-accessible medium can be programmed to generate a video overlay which can highlight (e.g., using any color), and/or otherwise identify various anatomical structures in the video. The exemplary identification can include, for example, changing the brightness of particular anatomical structures, changing the color of the particular anatomical structure, flashing the particular anatomical structure, or any other suitable way to draw the attention of the surgeon to the anatomical structure. Surgeons or other medical professionals can also select their preference for the type of highlighting, and can change the highlighting in the video in real time. For example, the surgeon or another medical professional, using such exemplary system, method, and computer-accessible medium, can mark that gallbladder in blue, while marking the surrounding tissue in a different color.

Figure 5A:
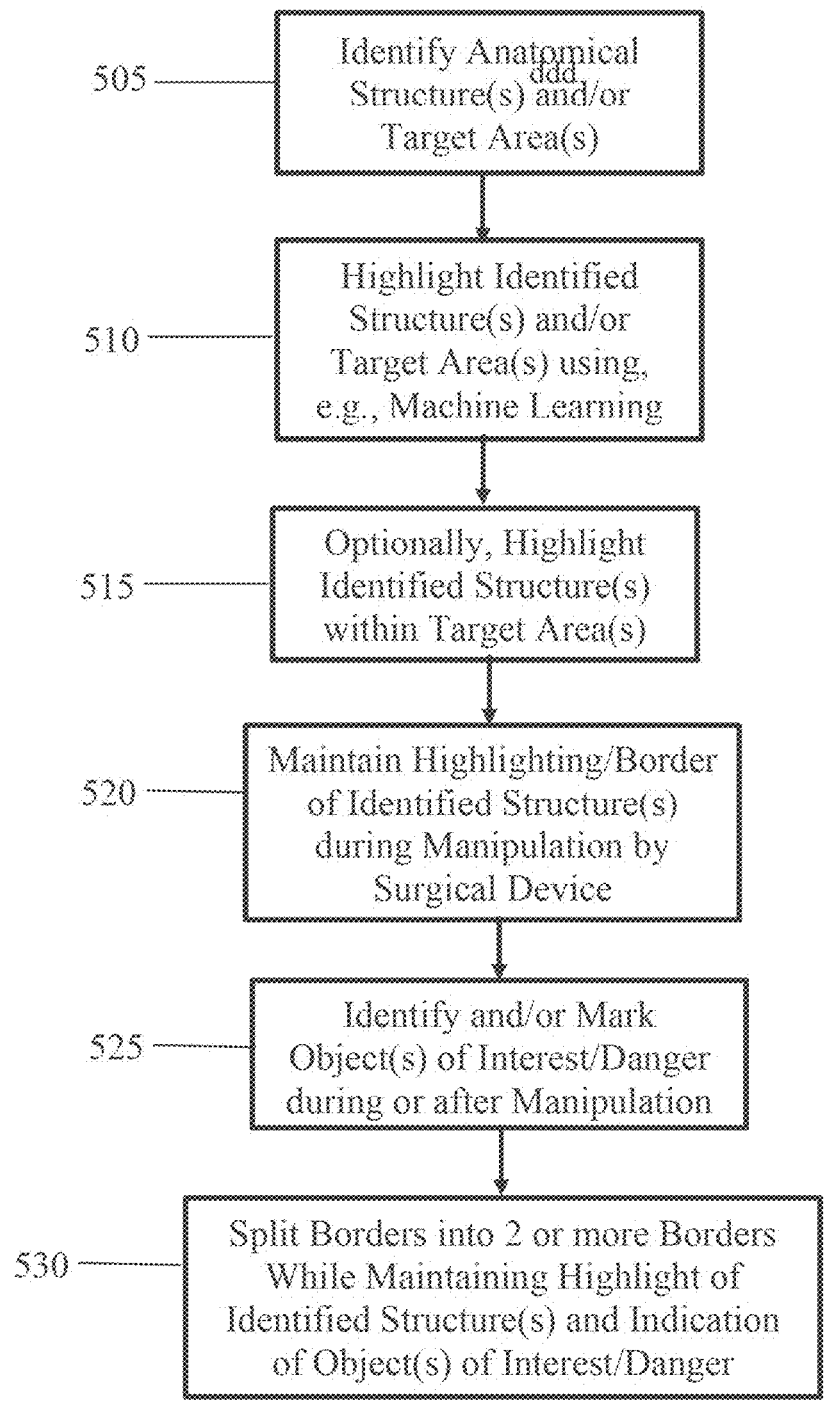
FIGS. 5A and 5B are exemplary diagrams illustrating an exemplary training of a semantic segmentation using machine learning procedures(s) according to an exemplary embodiment of the present disclosure.

For example, as shown in FIGS. 1 and 5A, one or more programmed computer processors used with and/or by the exemplary system, method, and computer-accessible medium has identified anatomical structures 105 and 110 (e.g., gallbladder 105 and cystic artery 110), as well as target area 115 (see procedure 505 of FIG. 5A). Gallbladder 105 has been highlighted by one or more programmed computer processors used with and/or by the exemplary system, method, and computer-accessible medium, using, for example, a machine learning procedure as discussed in further detail below. For example, a border 120 can be placed around target area 115, which can include a portion of gallbladder 105. Border 120 can be used to define the area of interest, or target area, for a target site. (See procedure 510 of FIG. 5A). Within the area of interest defined by border 120, target area 115 can also be highlighted for the surgeon (see procedure 515 of FIG. 5A). All of the anatomical structures shown in FIG. 1 can be manipulated by the surgeon using surgical tool 125.

The area of interest (e.g., the target zone and anatomical structures therein) and area of danger can be identified as a part of the video frame (e.g., using a pixel cloud) where the locations of the anatomical structures (e.g., cystic duct and cystic artery) can be estimated with the defined probability. One or more programmed computer processors used with and/or by exemplary system, method, and computer-accessible medium can determine the location probability of every pixel of the video frame. The target zone can be a pixel cloud in which every pixel can have a particular calculated location probability (e.g., of 0.7, or higher). The area of danger can depend on the surgical procedure being performed. For example, for gallbladder surgery, the area of danger can include a common bile duct, a common hepatic duct, a hepatic artery, or a portal vein, although not limited thereto.

Figure 2:

As shown in FIG. 2, surgical tool 125 can be used by the surgeon to manipulate gallbladder 105. As gallbladder 105 is manipulated (e.g., moved, rotated, etc.), one or more programmed computer processors used with and/or by the exemplary system, method, and computer-accessible medium can maintain the highlighting around gallbladder 105 (see procedure 520 of FIG. 5A). The programmed computer processor(s) used with and/or by the exemplary system, method, and computer-accessible medium can also maintain border 120 around the anatomical structure. As shown in FIG. 2, by manipulating gallbladder 105, the programmed computer processor(s) used with and/or by the exemplary system, method, and computer-accessible medium has identified and marked cystic artery 110 (see procedure 525 of FIG. 5A) using a punctate line 205, which can be predictive of Cystic artery before it can be visualized. This can include, for example, indicating to the surgeon or another medical professional the direction that cystic artery 110 runs (e.g., as indicated as being checkered in punctuate line 205 by the programmed computer processor(s) used with and/or by the exemplary system, method, and computer-accessible medium).

Figure 3:
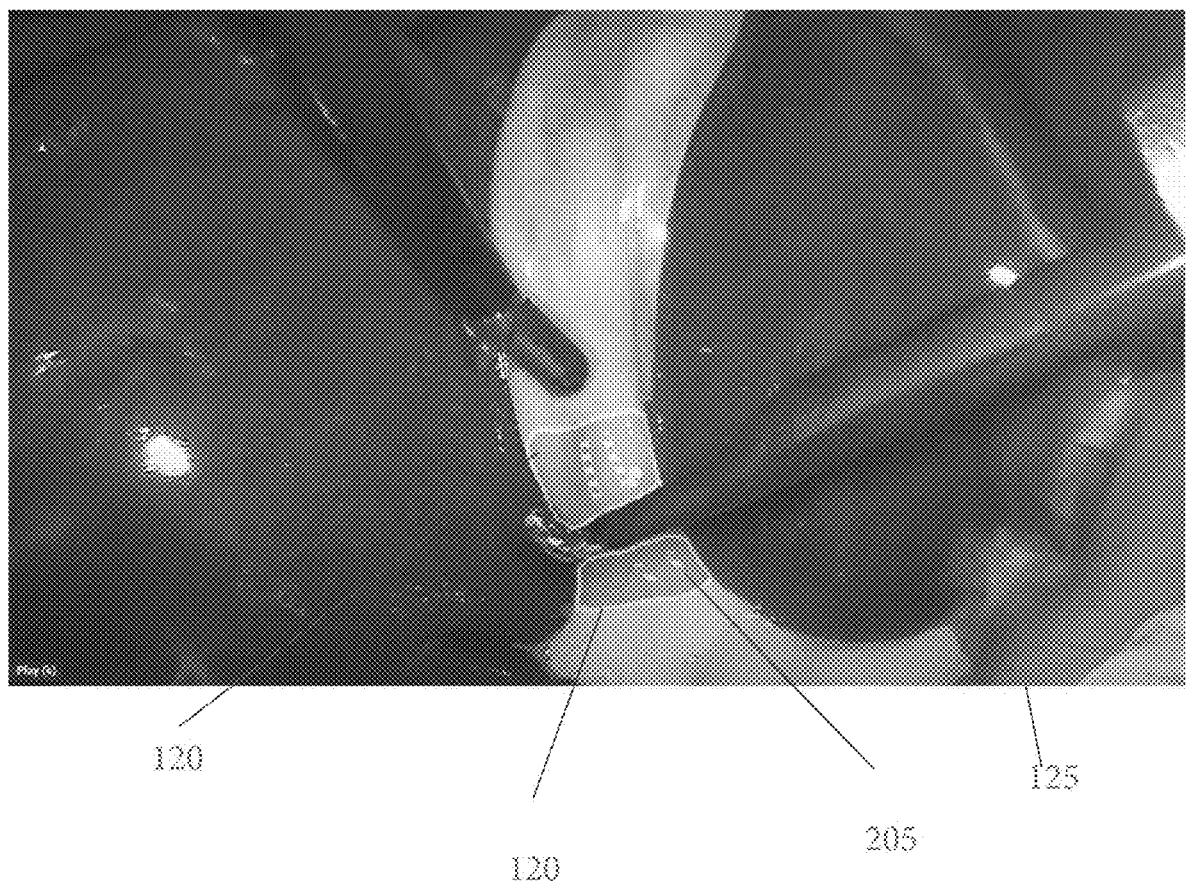
Figure 4:
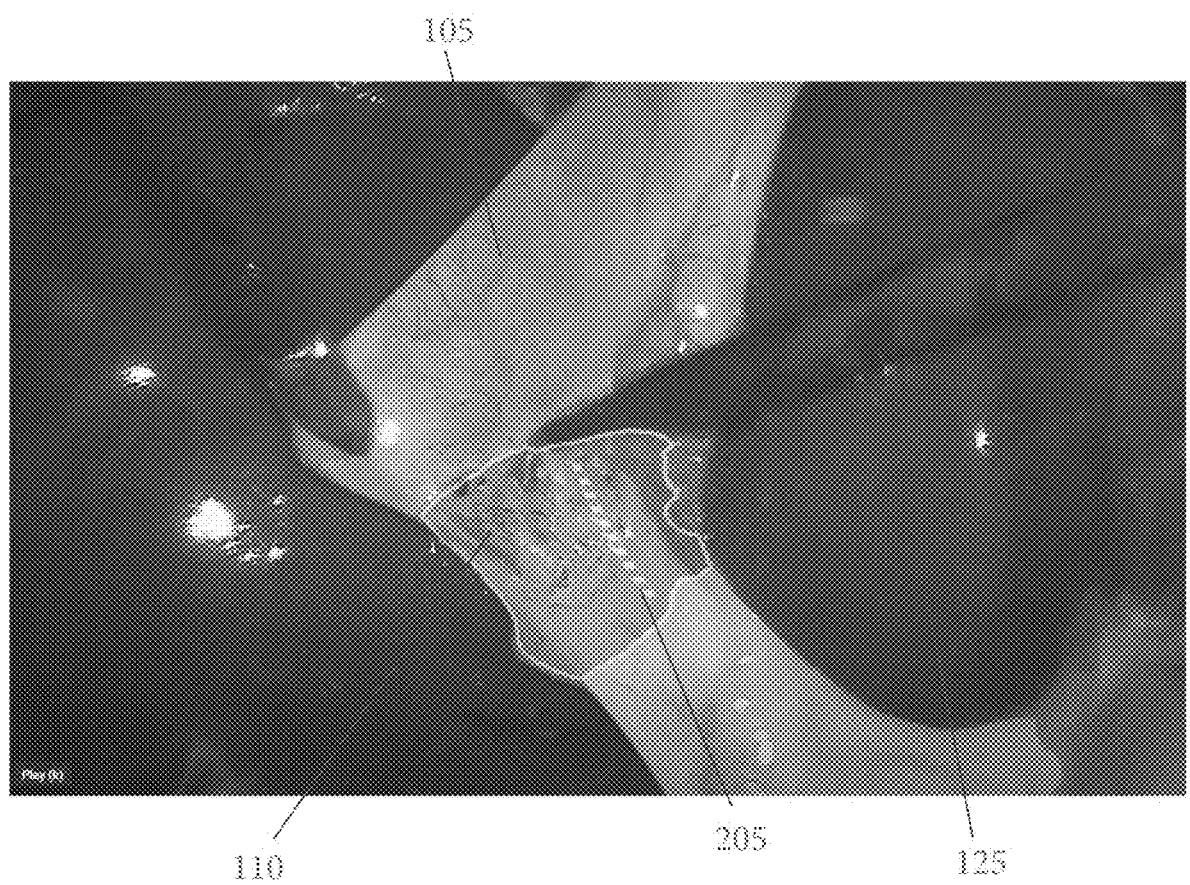

As shown in the exemplary image shown in FIG. 3, surgical tool 125 can manipulate gallbladder 105 further, and now obstructs part of gallbladder 105. The programmed computer processor(s) used with and/or by the exemplary system, method, and computer-accessible medium can split border 120 into two separate borders, while maintaining the highlighting of anatomical structure 105 and the indication of cystic artery 110 using punctuate line 205 (see procedure 530 of FIG. 5A). FIG. 4 shows an exemplary image illustrating further manipulation of gallbladder 105 using surgical tool 125.

As discussed above, the programmed computer processor(s) used with and/or by the exemplary system, method, and computer-accessible medium can generate a real time video overlay during using in a surgical procedure. For example, the programmed computer processor(s) used with and/or by the exemplary system, method, and computer-accessible medium can identify an area of interest (e.g., a region for the surgeon to operate in) and an area of danger (e.g., an area to avoid by the surgeon). The area of danger can include certain anatomical structures to be avoided, which can cause temporary or permanent injury to the patient. The video overlay can be continuously modified, in real time, using the machine learning procedure.

The area of interest and area of danger can be continuously updated by the exemplary system, method, and computer-accessible medium. The boundaries are can be updated at a particular number of frames per second (e.g., 50 video frames per second). The programmed computer processor(s) used with and/or by the exemplary system, method, and computer-accessible medium, according to an exemplary embodiment of the present disclosure can receive a video frame from a camera, and use the pretrained machine learning procedure in an "inference" mode to calculate the location probabilities of every pixel of the boundaries, and then calculate a bounding box for the pixel cloud for the pixels which have the calculated location or a particular probability (e.g., 0.7 or higher).

The exemplary programmed computer processor(s) used with and/or by the exemplary system, method, and computer-accessible medium can locate and/or identify anatomical structures that can be difficult for the surgeon to visualize. For example, the anatomical structures can be wholly or partially obscured from view, and the programmed computer processor(s) used with and/or by the exemplary system, method, and computer-accessible medium can identify or predict the location of these structures and mark them (e.g., using highlighting, a border, or any other suitable way of marking an anatomical structure as described above)—to assist the surgeon or another medical professional during an operation or a medical procedure. Further, the programmed computer processor(s) used with and/or by the exemplary system, method, and computer-accessible medium can be used to predict the location of these obstructed structures using the exemplary machine learning procedure as described below.

Exemplary Machine Learning Procedure

To process the video generated during the medical/surgical procedure, the computer processor(s) used with and/or by the exemplary system, method, and computer-accessible medium can be programmed and/or otherwise configured to utilize an exemplary machine learning procedure. For example, the exemplary machine learning procedure can be used to predict (i) the cystic artery with a mask, (ii) the cystic duct with a mask, and/or (iii) the location of the gallbladder, the target zone, and the danger zone with masks. The exemplary machine learning procedure can be and/or include deep Convolutional Neural Network ("CNN") for Semantic Segmentation tasks. For example, an exemplary U-Net architecture with ResNet34 backbone can be pretrained with, e.g., weight initializations. For the semantic segmentation model training and testing, the following exemplary datasets were used: (i) datasets containing frames from laparoscopic cholecystectomy videos, and (ii) datasets containing corresponding masks marked by surgeons. Any suitable dataset can be used based on the anatomy being trained on. The markup of the dataset can be performed automatically, semi-automatically, or manually.

For the cystic duct mask and the cystic artery mask, the exemplary training included 33635 frames from laparoscopic cholecystectomy videos and validation/testing included 15290 frames from laparoscopic cholecystectomy videos. For gallbladder, target zone, and danger zone masks, training included 27858 frames from laparoscopic cholecystectomy videos, and validation/testing included 12799 frames from laparoscopic cholecystectomy videos. It should be understood that other exemplary training parameters, inputs and/or procedures can be utilized within the scope of the exemplary embodiments of the present disclosure.

For example, during the training process, the input frames can be modified and/or augmented. The exemplary augmentation can include, e.g., (i) shifting vertically and/or horizontally (e.g., by +40%), (ii) scaling (e.g., by +−15%), (iii) shearing (e.g., by +−5%), (iv) rotating (e.g., by)+−30°, (v) flipping flipped horizontally (e.g., with a probability 0.50), (vi) changing brightness (e.g., by +−30%), and/or (vii)

cutting out in random places, except cystic artery location, from 1 up to 5 patches (e.g., replaced with gray color) of size 0.2 corresponding to image size.

Figure 5B:
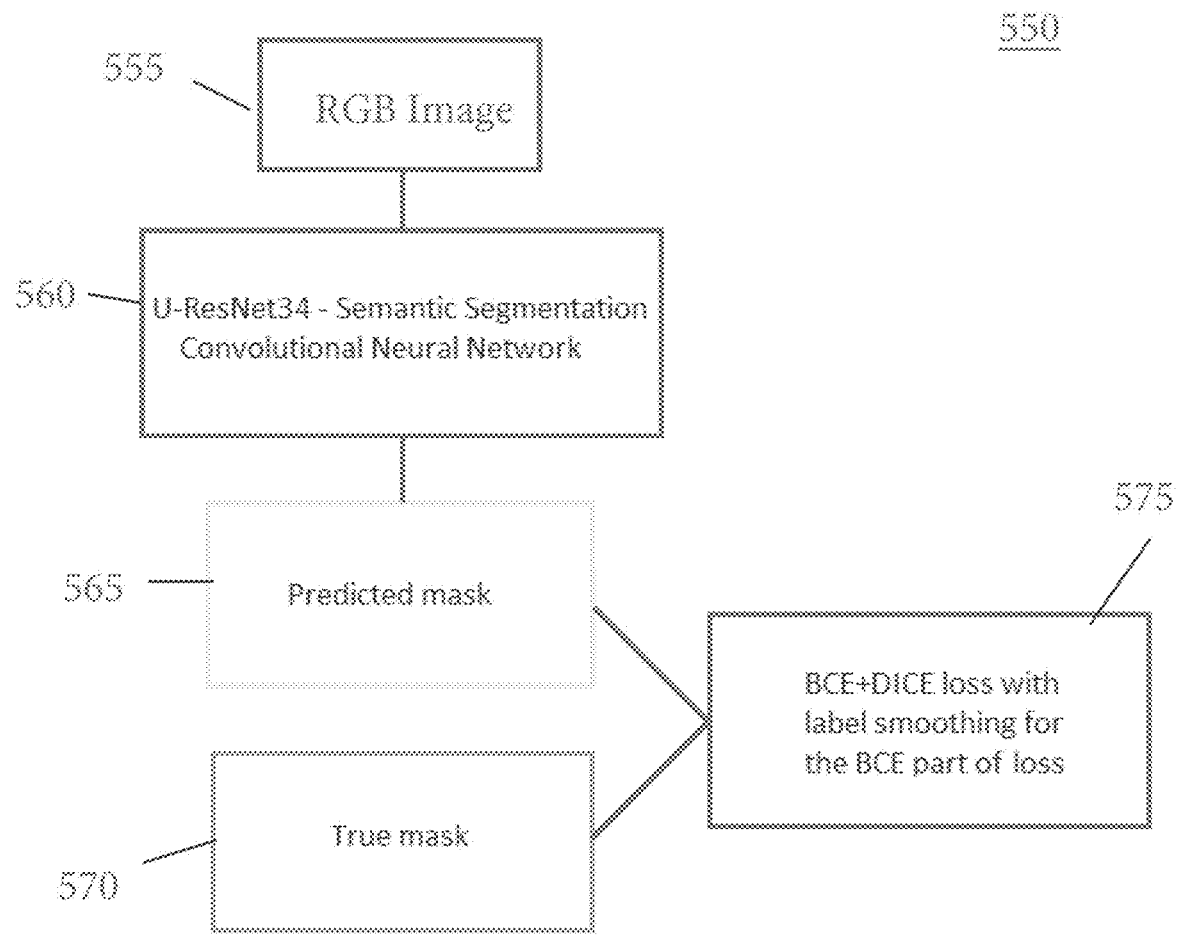

FIG. 5B shows a diagram illustrating the exemplary training 550 of semantic segmentation using machine learning according to an exemplary embodiment of the present disclosure. For example, one or more RGB mages 555 can be input into the exemplary machine learning procedure 560 (e.g., which can be a U-ResNet 34—Semantic Segmentation Convolutional Neural Network). The output of the exemplary machine learning procedure can be a predicted mask 565. The predicted mask 565 and a true mask 570 can be used for Binary Cross Entropy ("BCE")+DICE loss with label smoothing for the BCE part of the loss. For example, BCE is a binary classification loss functions, which can be referred to as the "Log loss function." The DICE score, or the F1 score, is a measure of a test's accuracy –. For DICE loss=1—DICE score, the more accuracy, the less the loss. For the exemplary segmentation tasks, a weighted combination of these two loss functions can be used, which can be referred to as the BCE+DICE loss.

In Label smoothing, "hard" class labels (e.g., 0-1 for binary classification) can be replaced with "soft" class labels (e.g., 0.1-0.9). In certain exemplary situation(s), these exemplary class labels can be replaced with random ones from a particular range. Such exemplary configuration can prevent and/or reduce overfitting on incorrect labelling, as losses on such labels will be less. This can be beneficial because the exemplary masks can be "dancing," and it may not always possible to determine the exact location of where the mask ends, and not just above/below.

For the exemplary the binary segmentation problem, 1*BCE+1*DICE loss can be used, and in BCE loss, labels 0.2-0.8 (e.g., label smoothing=0.2) can be used instead of we have labels 0-1. For the exemplary procedure of multiclass segmentation, 1*CCE+1*DICE loss can be used, and in CCE label smoothing, 0.1 can be used. Thus, the exemplary labels can be, for example:

$$1 \rightarrow (1-0.1)*1+0.1/4=0.9+0.025=0.925$$

$$0 \rightarrow (1-0.1)*0+0.1/4=0.025$$

Figure 6:
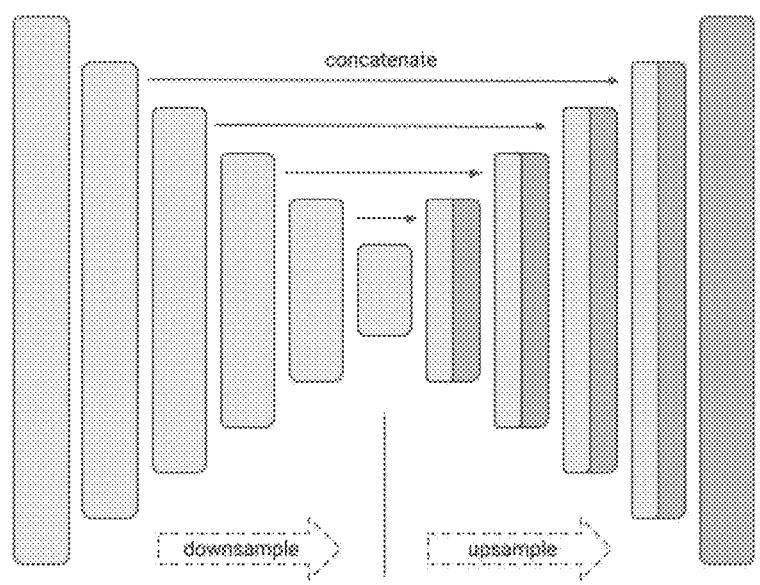
FIG. 6 is an exemplary diagram of an architecture and/or procedure of the exemplary neural network which can be used to generate the video overlay shown in FIGS. 1-4 according to an exemplary embodiment of the present disclosure.

FIG. 6 shows an exemplary diagram of architecture 600 of the exemplary neural network used to generate the video overlay shown in FIGS. 1-4 according to an exemplary embodiment of the present disclosure. In particular, the video overlay can be generate using a U-net type architecture, as shown in FIG. 6.

The exemplary machine learning which can be implemented in accordance with the exemplary embodiments of the present disclosure can utilize information related to previous surgical procedures in order to be trained. The exemplary system, method, and computer-accessible medium can then be applied to a particular surgical procedure. The programmed computer processor(s) used with and/or by the exemplary system, method, and computer-accessible medium can utilize various neural networks, such as, e.g., CNN and/or recurrent neural networks ("RNN") to generate the exemplary model. A CNN can include one or more convolutional layers (e.g., with a subsampling step) and then followed by one or more fully connected layers. CNNs can utilize local connections, and can have tied weights followed by some form of pooling which can result in translation invariant features.

For example, RNN is a class of artificial neural network where connections between nodes form a directed graph along a sequence. This can facilitate the determination of temporal dynamic behavior for a time sequence. Unlike feedforward neural networks, RNNs can use their internal state (e.g., memory) to process sequences of inputs. A RNN can generally refer to two broad classes of networks with a similar general structure, where one is finite impulse and the other is infinite impulse. Both classes of networks can exhibit temporal dynamic behavior. A finite impulse recurrent network can be, or can include, a directed acyclic graph that can be unrolled and replaced with a strictly feedforward neural network, while an infinite impulse recurrent network can be, or can include, a directed cyclic graph that may not be unrolled. Both finite impulse and infinite impulse recurrent networks can have additional stored states, and the storage can be under the direct control of the neural network. The storage can also be replaced by another network or graph, which can incorporate time delays or can have feedback loops. Such controlled states can be referred to as gated state or gated memory, and can be part of long short-term memory networks ("LSTMs") and gated recurrent units RNNs can be similar to a network of neuron-like nodes organized into successive "layers," each node in a given layer being connected with a directed (e.g., one-way) connection to every other node in the next successive layer. Each node (e.g., neuron) can have a time-varying real-valued activation. Each connection (e.g., synapse) can have a modifiable real-valued weight. Nodes can either be (i) input nodes (e.g., receiving data from outside the network), (ii) output nodes (e.g., yielding results), and/or (iii) hidden nodes (e.g., that can modify the data en route from input to output). RNNs can accept an input vector x and give an output vector y. However, the output vectors are based not only by the input just provided in, but also on the entire history of inputs that have been provided in in the past.

For supervised learning in discrete time settings, sequences of real-valued input vectors can arrive at the input nodes, one vector at a time. At any given time step, each non-input unit can compute or otherwise determine its current activation (e.g., result) as a nonlinear function of the weighted sum of the activations of all units that connect to it. Supervisor-given target activations can be supplied for some output units at certain time steps. For example, if the input sequence is a speech signal corresponding to a spoken digit, the final target output at the end of the sequence can be a label classifying the digit. In reinforcement learning settings, no teacher provides target signals. Instead, a fitness function, or reward function, can be used to evaluate the RNNs performance, which can influence its input stream through output units connected to actuators that can affect the environment. Each sequence can produce an error as the sum of the deviations of all target signals from the corresponding activations computed by the network. For a training set of numerous sequences, the total error can be the sum of the errors of all individual sequences.

The programmed computer processor(s) used with and/or by the exemplary system, method, and computer-accessible medium can also employ hierarchical clustering, collaborative filtering, content-based filtering, or any other suitable machine learning procedure.

Exemplary Scoring/Metrics

The quality assessment of the exemplary machine learning procedure can performed at two stages by using different metrics/scoring approaches. Stage 1 can be or include the validation/test metrics during the training process. The better the metrics are, the better the exemplary machine learning procedure can be. The following exemplary quality metrics can be collected and accessed for stage 1: (i)

Validation/Testing loss—BCE+DICE (e.g., the lower the better), and (ii) Validation/Testing accuracy—F1 score with and without background (e.g., the higher the better). An exemplary version of the exemplary machine learning procedure (e.g., checkpoint) having the best values can be selected. Any suitable loss function can be used including, but not limited to, mean squared error, balanced cross entropy, and focal loss. During stage 2, the video processed using the exemplary machine learning procedure can be recorded with subsequent visual evaluations.

Exemplary Safe Markers

Figure 7:
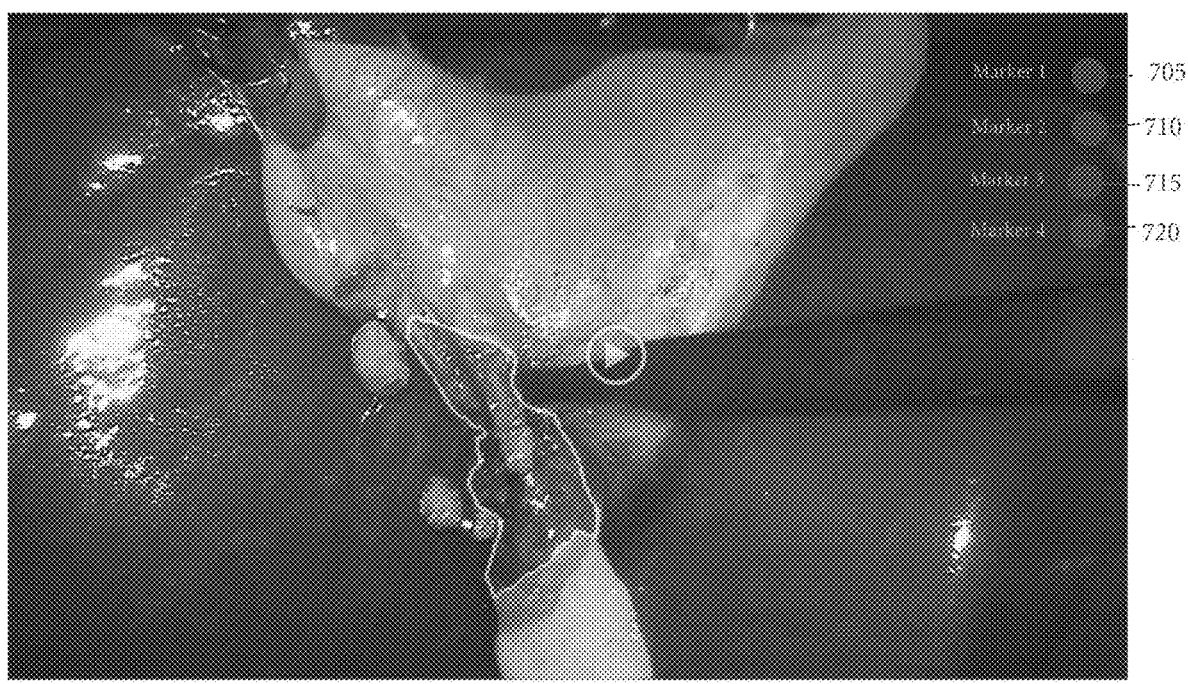
FIGS. 7-9 are exemplary images of the video overlay providing a safe-to-proceed indication according to an exemplary embodiment of the present disclosure.
Figure 8:
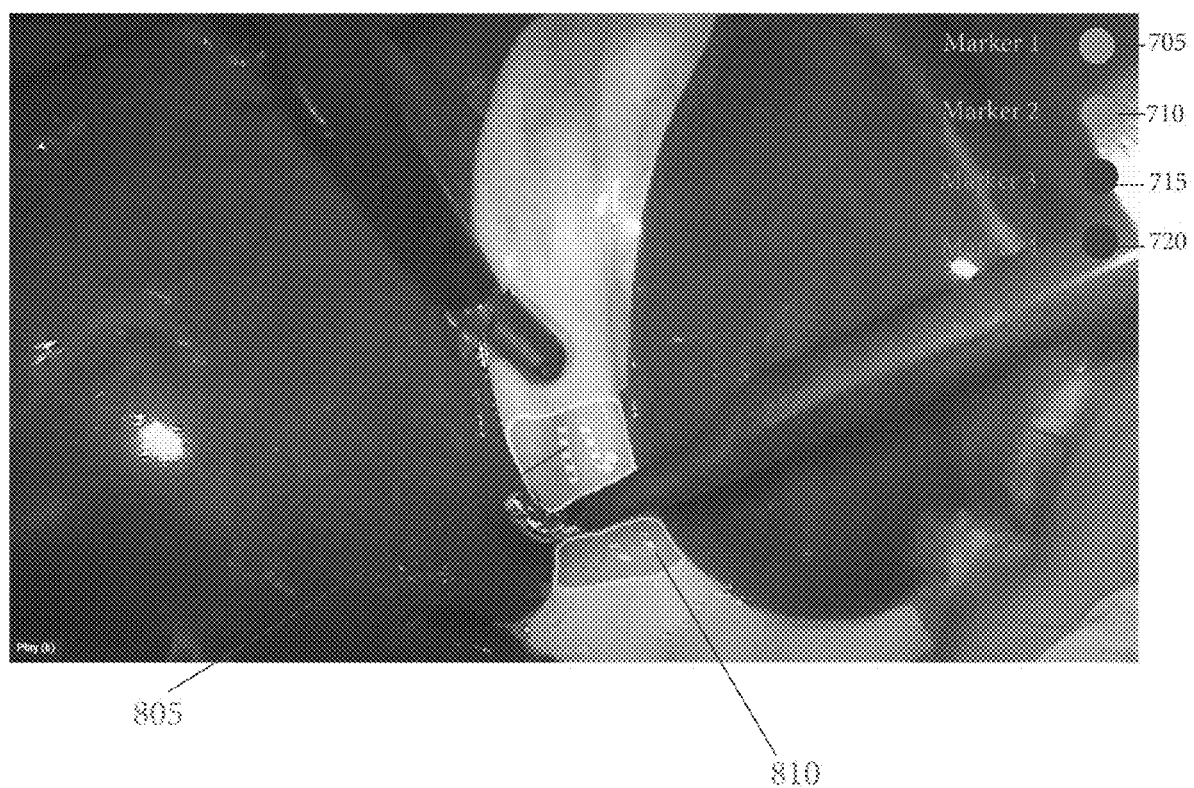
Figure 9:
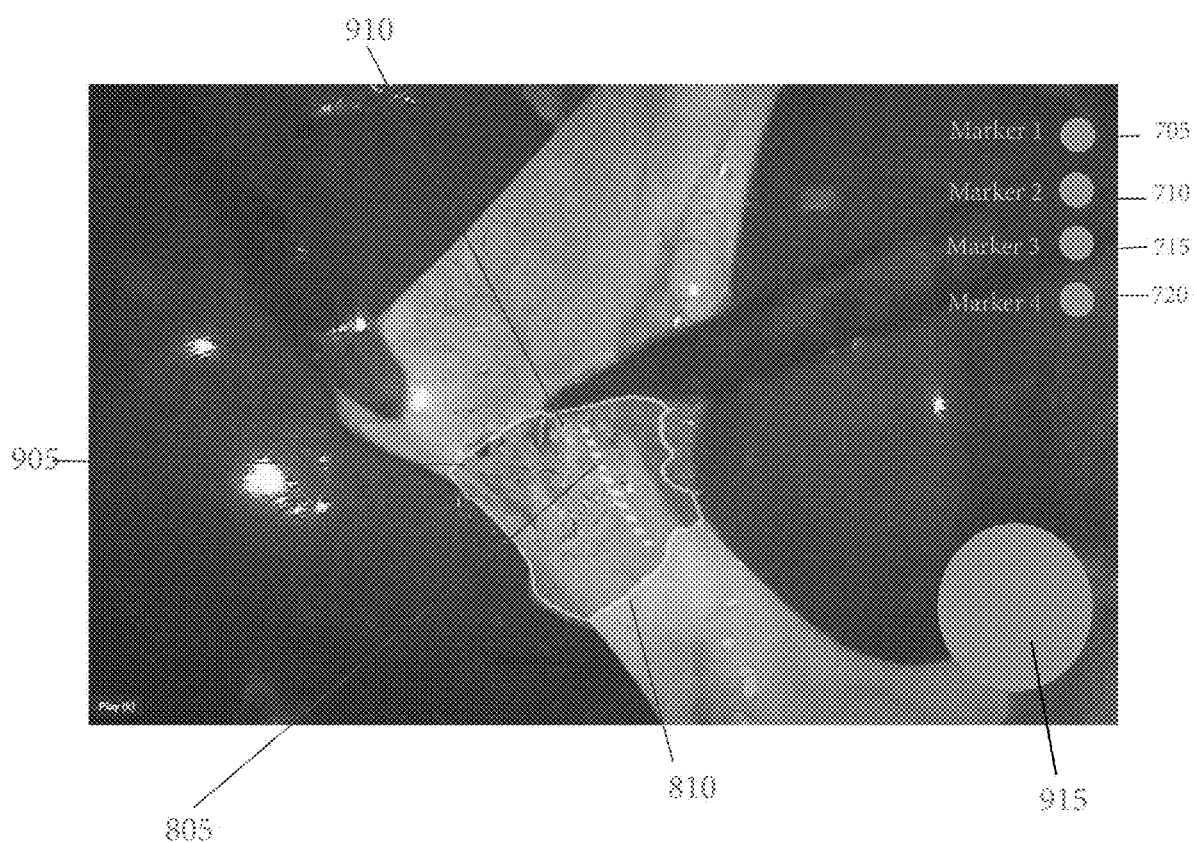

FIGS. 7-9 show exemplary images of the video overlay providing a safe to proceed indication to the surgeon or another medical professional according to an exemplary embodiment of the present disclosure. In particular, the programmed computer processor(s) used with and/or by the exemplary system, method, and computer-accessible medium can analyze the live video from a surgical procedure to determine the presence or absence of particular markers needed to proceed during the surgery. For example, during a surgical procedure, the surgeon or medical professional may need to locate and/or visualize certain anatomical structures before proceeding (e.g., before making an incision or cutting an anatomical structure). The location or visualization of the particular structures can facilitate the surgeon/medical professional to avoid these structures during the procedure in order to avoid inadvertently injuring the patient. These structures, e.g., when unmarked, can be difficult to keep track of by the surgeon. Additionally, as discussed herein, certain structures can be partially, or wholly, obscured from the view of the surgeon/medical professional during an operation and/or a medical procedure. The programmed computer processor(s) used with and/or by the exemplary system, method, and computer-accessible medium can track the structures using, e.g., markers the surgical procedure/operation.

Various different markers can be used, which can be based on the surgical/medical procedure being performed. For example, prior to the surgical procedure being performed, the exemplary system, method, and computer-accessible medium can be provided with information on the surgical procedure (e.g., the type, what is being performed, etc.). The programmed computer processor(s) used with and/or by the exemplary system, method, and computer-accessible medium can access a database that includes markers associated with the surgical procedure. The database can be a local database (e.g., a non-networked database accessible by the exemplary system, method, and computer-accessible medium). Alternatively, the database can be a network or cloud-based database that is accessed by the exemplary system, method, and computer-accessible medium prior to the surgical procedure.

Markers can also be patient specific. For example, markers can change if the patient is male or female. Markers can also be age specific. For example, markers for children can be different from markers for adults. Markers can also be different for older children versus younger children. After the programmed computer processor(s) used with and/or by the exemplary system, method, and computer-accessible medium has determined the markers associated with a specific surgical procedure, the such exemplary programmed processor(s) can determine the age and gender of the patient (e.g., by receiving the information from a doctor, nurse, or other medical professional). The programmed computer processor(s) used with and/or by the exemplary system, method, and computer-accessible medium, according to an exemplary embodiment of the present disclosure can then update the markers based on the age and/or gender of the patient.

Instead of determining the markers based on a database, the exemplary programmed computer processor(s) used with and/or by the exemplary system, method, and computer-accessible medium can determine the markers by automatically analyzing the video feed. For example, the exemplary programmed computer processor(s) can identify some or all of the anatomical structures that are present in the video feed. Based on the identified anatomical structure, the exemplary programmed computer processor(s) can determine one or more possible surgical procedures being performed, and then automatically determine markers associated with the surgical procedure. The exemplary programmed computer processor(s) can then verify the surgical procedure being performed (e.g., by prompting a medical professional for confirmation).

Markers can also be manual set or adjusted by the surgeon performing the surgical procedure. For example, the exemplary programmed computer processor(s) used by and/or with the exemplary system, method, and computer-accessible medium can determine an initial set of markers, and provide the initial set of markers to the surgeon. The surgeon can review the initial set of markers and either confirm or modify the markers. For example, the exemplary programmed computer processor(s) can determine that five markers are needed for a particular surgery. This information can be provided to the surgeon. The surgeon/medical professional can review the markers, and make any changes (e.g., adding an additional marker, or removing one of the five markers). The surgeon/medical professional can also identify markers as being necessary to proceed and beneficial to proceed. For example, if the exemplary programmed computer processor(s) has identified six markers, the surgeon/medical professional may only actually need four markers in order to proceed. The surgeon/medical professional can review all six identified markers, and indicate which ones are necessary and which ones are only beneficial. Based on this indication from the surgeon/medical professional, the exemplary programmed computer processor(s) can display all markers identified, but then mark certain ones as necessary and certain ones as beneficial (e.g., as indicated by the surgeon/medical professional) or only display the necessary markers.

For example, as show in FIG. 7, an exemplary image of the video overlay can be provided indicating four safe to proceed markers 705, 710, 715, and 720. Each marker 705-720 can have an associated description, which can provide information to the surgeon on what the specific marker refers to. For example, marker 705 can represent a vein and marker 710 can represent a nerve. As shown in FIG. 7, markers 705-720 are all one color (e.g., red), indicating that the exemplary system, method, and computer-accessible medium has not located the markers. FIG. 8 shows an exemplary image in which exemplary programmed computer processor(s) used by or with the exemplary system, method, and computer-accessible medium has identified two markers (e.g., markers 705 and 710). Markers 705 and 710 can be associated with anatomical structures 805 and 810, respectively. The color associated with markers 705 and 710 can change (e.g., from red to green) to indicate to the surgeon that these markers have been identified. The surgeon/medical professional can then proceed further (e.g., performing additional incisions, or removing tissue) until all of the markers (e.g., markers 705-720) have been identified by the exemplary system, method, and computer-accessible medium. As the surgeon/medical professional proceeds with the surgery/medical procedure, it can be possible that a marker previously identified by the exemplary system, method, and computer-accessible medium can no longer be identified. In such a case, the marker can revert back to the original color (e.g., red) indicating that the exemplary programmed computer processor(s) can no longer identify the specific marker.

FIG. 9 shows an exemplary image where all markers 705-720 have been identified. For example, markers 715 and 720, which can correspond to anatomical structures 905 and 910, respectively, have then been identified by the exemplary programmed computer processor(s) used by or with the exemplary system, method, and computer-accessible medium. The color associated with markers 715 and 720 has been changed (e.g., from red to green), indicating that these markers have been identified. A large indicator (e.g., indicator 915) can be provided, which can indicate to the surgeon/medical professional that it is safe to proceed with the next part of the surgery/medical procedure.

Surgeries/medical procedures can vary in time and scope. For example, some surgeries are simple, and may only take 30 minutes, while complicated surgeries can take many hours. A simple surgery/medical procedure may have a single set of safe-to-proceed markers. Thus, one the single set of safe to proceed markers have all been identified, and the surgeon/medical professional initiates a particular action based on the singe set of safe to proceed markers, then no more markers are needed during the surgery/medical procedure. However, for complex surgeries/medical procedures, many different set of markers can be needed. For example, an initial set of markers can be determined by the exemplary programmed computer processor(s) that is used by or with the exemplary system, method, and computer-accessible medium and can be provided to the surgeon/ medical professional. Once most or all of the markers have been identified by the exemplary system, method, and computer-accessible medium, the surgeon can proceed to the next step or phase in the surgical procedure. The surgeon/ medical professional can provide an indication to the exemplary programmed computer processor(s) used by or with the procedure has proceeded to the next step, or the exemplary programmed computer processor(s) used by or with can automatically determine that the procedure has proceeded to the next step by analyzing the actions performed by the surgeon/medical professional. A new set of markers can then be provided to the surgeon, which can be based on the next step in the procedure. The new set of markers can include some of the markers from previous sets of markers, or the new set of markers can include only new markers.

The exemplary programmed computer processor(s) used by or with the exemplary system, method, and computer-accessible medium can also provide the surgeon/medical professional with recommended steps on how the markers can be identified. For example, by analyzing the video feed from the surgery, the exemplary programmed computer processor(s) used by or with can provide a recommendation on where to make an incision, or what tissue to remove, in order for the exemplary programmed computer processor(s) used by or with to identify specific markers. The recommended steps can be constantly, and automatically, updated based on the markers already identified, and the steps the surgeon has already taken to have the markers identified.

As shown in FIGS. 7-9, markers 705-720 can be provided as part of the video overlay. Alternatively or in addition, markers 705-720 can be provided on a separate video screen so as to not interfere with the surgeon's view of the procedure.

Figure 10:
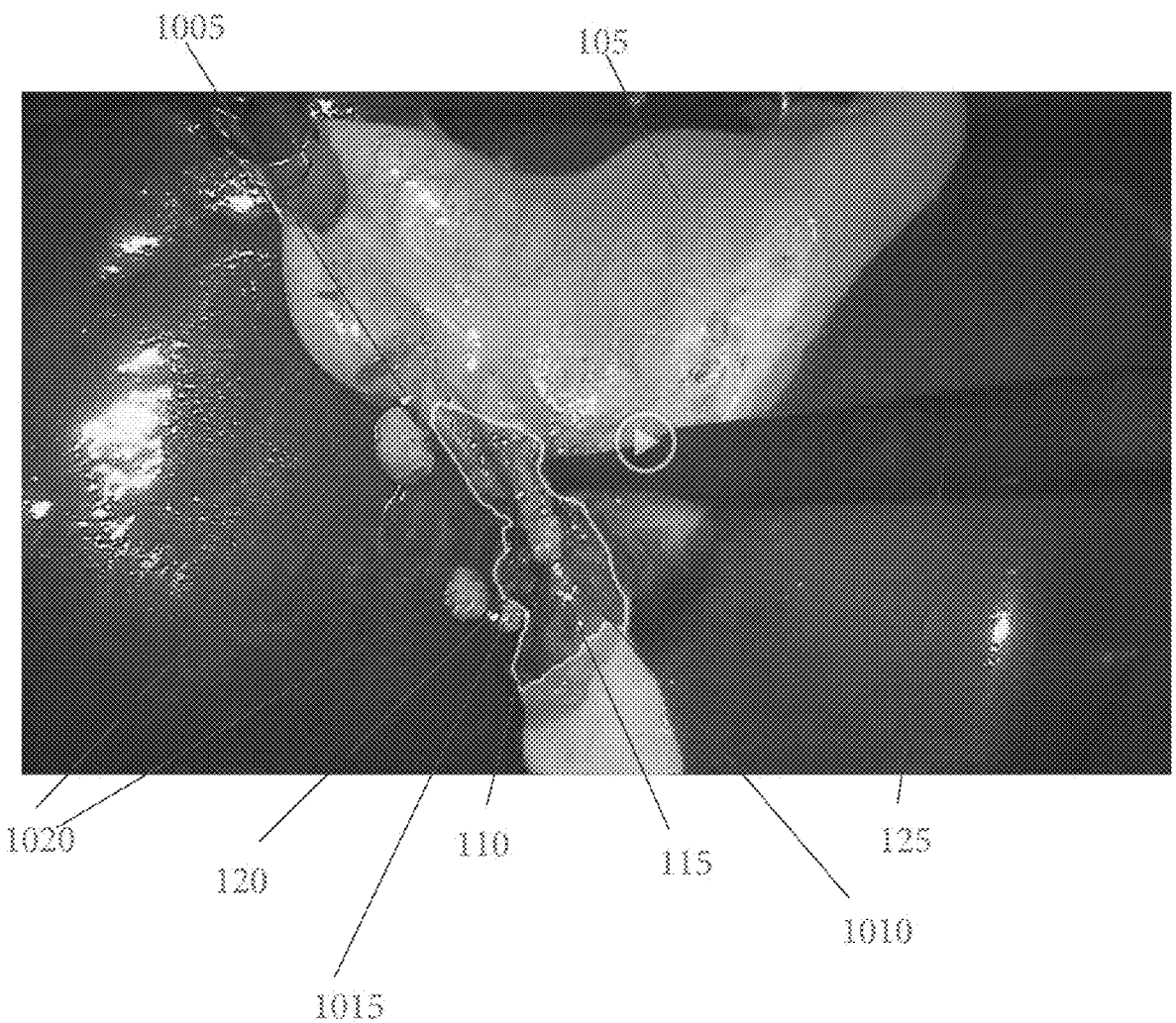
FIG. 10 is an exemplary image of the video overlay generated in FIG. 1 with various markers identified therein according to an exemplary embodiment of the present disclosure.

FIG. 10 shows an exemplary image of the video overlay generated in FIG. 1 with various exemplary markers identified therein according to an exemplary embodiment of the present disclosure. For example, FIG. 10 illustrates four markers (e.g., clips 1005, 1010, and 115) and transected cystic duct 1020. The area of interest can include (i) a target area (e.g., where surgical manipulations can take place) and (ii) a danger area (e.g., in the vicinity of the target area, where surgical manipulations should be avoided in order avoid injury to significant bystander structures. The anatomic structures of significance within Target area, which are to be dissected, can be identified, and critically, or irreversibly, affected (e.g., transected). Examples of such anatomical structures during cholecystectomy can be the cystic duct (e.g., cystic duct 1020), where the cystic duct can be clipped using clips 1005, 1010, and 1015.

For example, a minimum number of markers can be used to indicate a safe to proceed for the surgeon. However, guiding markers can also be used (e.g., to assist a surgeon in the decision making during surgery) with a certain/sufficiently high degree of accuracy based on the exemplary system, method, and computer-accessible medium. In certain exemplary procedures, a single marker can be used, which can aid in increasing safety. In other exemplary procedures, more markers can be used. Additionally, the experience of the surgeon performing the surgery can be used in determining the minimum number of markers. As an example, for a less experienced surgeon, or for an experienced but cognitively impaired surgeon (e.g., tired, stressed etc.) it can be beneficial to mark all of (i) the target area, (ii) the danger area, and (iii) all anatomical structures, which are planned to be significantly manipulated during surgery. The amount of these structures can be 1 or more. The more of these structures that are marked, the potentially safer an operation can be.

Figure 11:
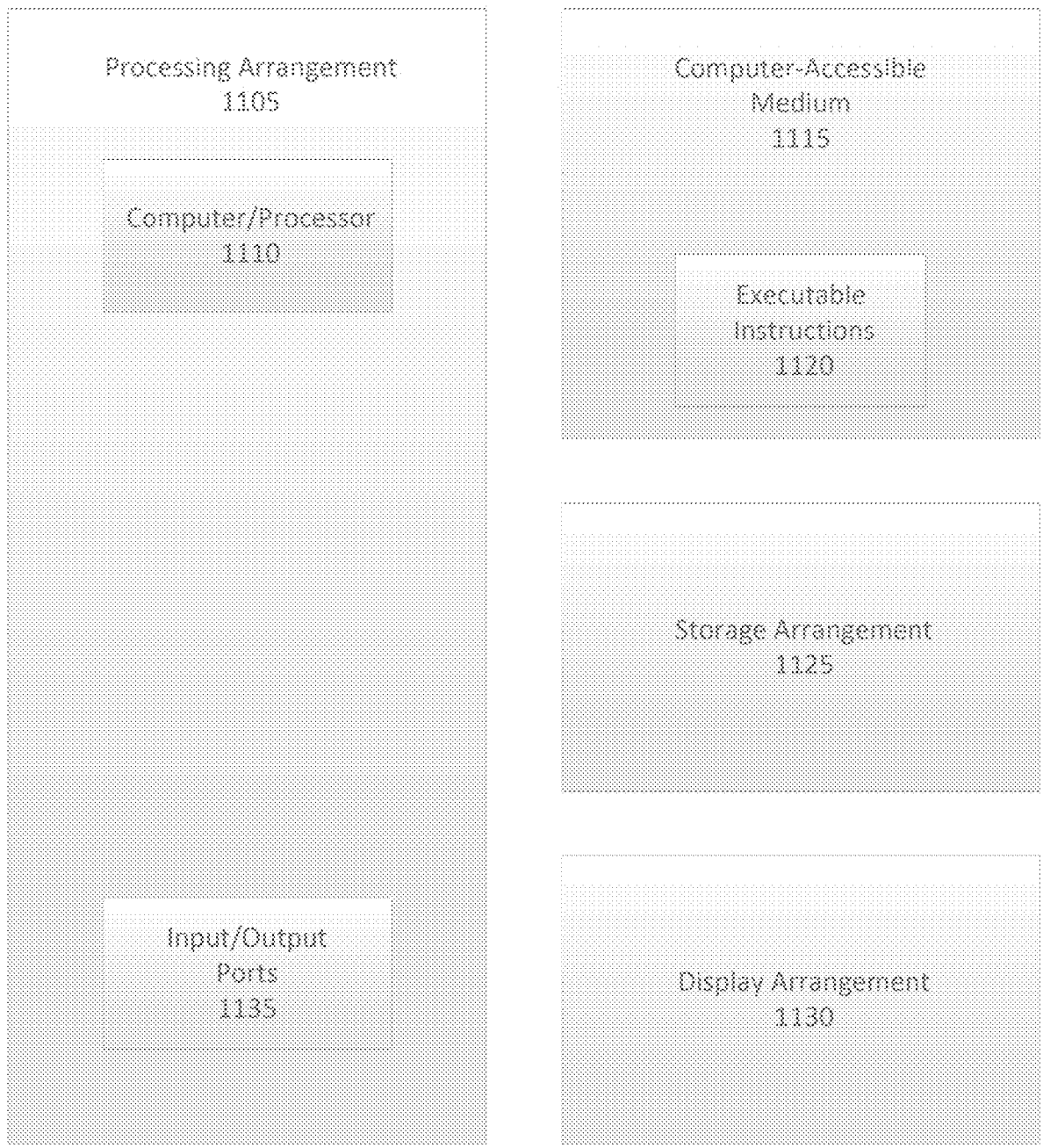
FIG. 11 is an illustration of an exemplary block diagram of an exemplary system in accordance with certain exemplary embodiments of the present disclosure.

FIG. 11 shows a block diagram of an exemplary embodiment of a system according to the present disclosure, which can be utilized by the exemplary system, method, and computer-accessible medium in order to analyze the live video from a medical procedure and provide a video overlay using, for example, a machine learning procedure. For example, exemplary procedures used by the exemplary system, method, and computer-accessible medium in accordance with the present disclosure described herein can be performed by a processing arrangement and/or a computing arrangement (e.g., computer hardware arrangement) 1105. Such processing/computing arrangement 1105 can be, for example entirely or a part of, or include, but not limited to, a computer/processor 1110 that can include, for example one or more microprocessors, and use instructions stored on a computer-accessible medium (e.g., RAM, ROM, hard drive, or other storage device).

As shown in FIG. 11, for example a computer-accessible medium 1115 (e.g., as described herein above, a storage device such as a hard disk, floppy disk, memory stick, CD-ROM, RAM, ROM, etc., or a collection thereof) can be provided (e.g., in communication with the processing arrangement 1105). The computer-accessible medium 1115 can contain executable instructions 1120 thereon. In addition or alternatively, a storage arrangement 1125 can be provided separately from the computer-accessible medium 1115, which can provide the instructions to the processing arrangement 1105 so as to configure the processing arrangement to execute certain exemplary procedures, processes, and methods, as described herein above, for example.

Further, the exemplary processing arrangement 1105 can be provided with or include an input/output ports 1135, which can include, for example a wired network, a wireless network, the internet, an intranet, a data collection probe, a sensor, etc. As shown in FIG. 11, the exemplary processing arrangement 1105 can be in communication with an exemplary display arrangement 1130, which, according to certain exemplary embodiments of the present disclosure, can be a touch-screen configured for inputting information to the processing arrangement in addition to outputting information from the processing arrangement, for example. Further, the exemplary display arrangement 1130 and/or a storage arrangement 1125 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A non-transitory computer-accessible medium having stored thereon computer-executable instructions for providing a video overlay during at least one medical procedure performed on at least one patient, wherein, when a computing arrangement executes the instructions, the computing arrangement is configured to perform procedures comprising:
   receiving at least one live video of the at least one medical procedure performed on the at least one patient;
   training a convolutional neural network to generate a training output that includes a predicted mask, wherein training dataset inputs include one or more RGB images including at least one mask marked by at least one medical professional;
   reducing cross entropy by employing Binary Cross Entropy with label smoothing using the predicted mask and a true mask, wherein at least one hard class label is replaced with at least one soft label;
   identifying, in real time, at least one target area and at least one area of danger on a surface or in at least one anatomical structure of the at least one patient by applying the training output to the at least one live video; and
   providing the video overlay based on the identification of the at least one target area and the at least one area of danger.

2. The computer-accessible medium according to claim 1, wherein the computing arrangement is further configured to continuously modify the video overlay, in real-time, using the convolutional neural network.

3. The computer-accessible medium according to claim 1, wherein the at least one medical procedure is a gallbladder surgery.

4. The computer-accessible medium according to claim 1, wherein the computer arrangement is configured to further train the convolutional neural network using at least one of (i) a plurality of further videos, or (ii) a plurality of images.

5. The computer-accessible medium according to claim 4, wherein the computer arrangement is further configured to at least one of (i) shift frames in the at least one of the plurality of further videos or the plurality of images, (ii) scale the frames in the at least one of the plurality of further videos or the plurality of images, (iii) shear the frames in the at least one of the plurality of further videos or the plurality of images, (iv) rotate the frames in the at least one of the plurality of further videos or the plurality of images, or (v) flip the frames in the at least one of the plurality of further videos or the plurality of images.

6. The computer-accessible medium according to claim 1, wherein the computer arrangement is further configured to identify the at least one anatomical structure that is believed to be safe to manipulate in the at least one live video using the convolutional neural network.

7. The computer-accessible medium according to claim 1, wherein the computer arrangement is further configured to determine at least one marker associated with the at least one medical procedure.

8. The computer-accessible medium according to claim 7, wherein the computer arrangement is further configured to provide an indication to at least one medical professional based on the at least one marker.

9. The computer-accessible medium according to claim 8, wherein the indication is (i) a safe-to-proceed indication if the at least one marker is detected, or (ii) a not-safe-to-proceed indication if the at least one marker is not detected.

10. A system for providing a video overlay during at least one medical procedure performed on at least one patient, comprising:
    at least one computer storage arrangement;
    at least one computer processor arrangement which (i) cooperates with the at least one computer storage arrangement, and (ii) configured to:
      receive at least one live video of the at least one medical procedure performed on the at least one patient;
      train a convolutional neural network to generate a training output that includes a predicted mask, wherein training dataset inputs include one or more RGB images including at least one mask marked by at least one medical professional;
      reduce cross entropy by employing Binary Cross Entropy with label smoothing using the predicted mask and a true mask, wherein at least one hard class label is replaced with at least one soft label;
      identify, in real time, at least one target area and at least one area of danger on a surface or in at least one anatomical structure of the at least one patient by applying the training output to the at least one live video; and
      provide the video overlay based on the identification of the at least one target area and the at least one area of danger.

11. A method for providing a video overlay during at least one medical procedure performed on at least one patient, comprising:
  receiving at least one live video of the at least one medical procedure performed on the at least one patient;
  training a convolutional neural network to generate a training output that includes a predicted mask, wherein training dataset inputs include one or more RGB images including at least one mask marked by at least one medical professional;
  reducing cross entropy by employing Binary Cross Entropy with label smoothing using the predicted mask and a true mask, wherein at least one hard class label is replaced with at least one soft label;
  identifying, in real time, at least one target area and at least one area of danger on a surface or in at least one anatomical structure of the at least one patient by applying the training output to the at least one live video; and
  using a computer hardware arrangement, providing the video overlay based on the identification of the at least one target area and the at least one area of danger.

12. A non-transitory computer-accessible medium having stored thereon computer-executable instructions for providing a video overlay during at least one medical procedure performed on at least one patient, wherein, when a computing arrangement executes the instructions, the computing arrangement is configured to perform procedures comprising:
  receiving at least one live video of the at least one medical procedure performed on the at least one patient;
  training a convolutional neural network to generate a training output that includes a predicted mask, wherein training dataset inputs include one or more RGB images including at least one mask marked by at least one medical professional;
  reducing cross entropy by employing Binary Cross Entropy with label smoothing using the predicted mask and a true mask, wherein at least one hard class label is replaced with at least one soft label;
  identifying, in real time, a location of at least one anatomical structure which is at least partially or wholly obscured from at least one of (i) a human eye, or (ii) a visualization tool by applying the training output to the at least one live video; and
  providing the video overlay based on the identification of the at least one partially or wholly obscured anatomical structure.

13. The computer-accessible medium according to claim 12, wherein the identifying of the location of the at least one anatomical structure includes predicting the location of the at least one anatomical structure.

14. The computer-accessible medium according to claim 12, wherein the computing arrangement is further configured to continuously modify the video overlay, in real-time, using the convolutional neural network.

15. A system for providing a video overlay during at least one medical procedure performed on at least one patient, comprising:
  at least one computer storage arrangement;
  at least one computer processor arrangement which (i) cooperates with the at least one computer storage arrangement, and (ii) configured to:
    receive at least one live video of the at least one medical procedure performed on the at least one patient;
    train a convolutional neural network to generate a training output that includes a predicted mask, wherein training dataset inputs include one or more RGB images including at least one mask marked by at least one medical professional;
    reduce cross entropy by employing Binary Cross Entropy with label smoothing using the predicted mask and a true mask, wherein at least one hard class label is replaced with at least one soft label;
    identify, in real time, a location of at least one anatomical structure that is at least partially or wholly obscured from at least one of (i) a human eye, or (ii) a visualization tool by applying the training output to the at least one live video; and
    provide the video overlay based on the identification of the at least one partially or wholly obscured anatomical structure.

16. A method for providing a video overlay during at least one medical procedure performed on at least one patient, comprising:
  receiving at least one live video of the at least one medical procedure performed on the at least one patient;
  training a convolutional neural network to generate a training output that includes a predicted mask, wherein training dataset inputs include one or more RGB images including at least one mask marked by at least one medical professional;
  reducing cross entropy by employing Binary Cross Entropy with label smoothing using the predicted mask and a true mask, wherein at least one hard class label is replaced with at least one soft label;
  identifying, in real time, a location of at least one anatomical structure that is at least partially or wholly obscured from at least one of (i) a human eye, or (ii) a visualization tool by applying the training output to the at least one live video; and
  using a computer hardware arrangement, providing the video overlay based on the identification of the at least one partially or wholly obscured anatomical structure.

* * * * *